(12) United States Patent
Chen et al.

(10) Patent No.: US 7,384,778 B2
(45) Date of Patent: Jun. 10, 2008

(54) METHODS AND DEVICES FOR THE DETECTION OF PATHOGENIC MICROORGANISMS AND THEIR ANTIMICROBIAL SUSCEPTIBILITY

(75) Inventors: Chun-Ming Chen, Falmouth, ME (US); Charles Carpenter, Scarborough, ME (US); Haoyi Gu, Yarmouth, ME (US); Ali Naqui, Falmouth, ME (US); Gary Madsen, Falmouth, WI (US); Thomas O'Connor, Jr., Westbrook, ME (US); Katherine Jean Esty, Westbrook, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 295 days.

(21) Appl. No.: 10/340,569

(22) Filed: Jan. 9, 2003

(65) Prior Publication Data

US 2004/0005653 A1    Jan. 8, 2004

Related U.S. Application Data

(60) Provisional application No. 60/347,485, filed on Jan. 10, 2002.

(51) Int. Cl.
*C12M 1/34*    (2006.01)
*C12Q 1/04*    (2006.01)

(52) U.S. Cl. ..................... 435/287.1; 435/34
(58) Field of Classification Search .................. 435/4, 435/29, 32, 34, 38, 39, 252.1, 252.8, 253.6, 435/287.1, 848, 849
See application file for complete search history.

(56) References Cited

U.S. PATENT DOCUMENTS

| | | | |
|---|---|---|---|
| 3,832,532 A | 8/1974 | Praglin | |
| 4,236,211 A | 11/1980 | Arvesen | |
| 4,591,554 A | 5/1986 | Koumura et al. | |
| 4,919,894 A * | 4/1990 | Daniel | 422/104 |
| 4,925,789 A | 5/1990 | Edberg | |
| 5,064,756 A | 11/1991 | Carr et al. | |
| 5,236,827 A | 8/1993 | Sussman et al. | |
| 5,457,030 A | 10/1995 | Badal et al. | |
| 5,620,865 A | 4/1997 | Chen et al. | |
| 5,650,290 A * | 7/1997 | Grant | 435/34 |
| 5,922,593 A | 7/1999 | Livingston | |
| 6,090,541 A * | 7/2000 | Wicks et al. | 435/5 |
| 6,251,624 B1 * | 6/2001 | Matsumura et al. | 435/34 |
| 6,319,665 B1 | 11/2001 | Zwanziger et al. | |
| 6,387,650 B1 | 5/2002 | Townsend et al. | |
| 6,472,167 B1 | 10/2002 | Townsend et al. | |
| 6,984,499 B2 * | 1/2006 | Chen et al. | 435/34 |
| 2002/0146345 A1 * | 10/2002 | Neilson et al. | 422/51 |

FOREIGN PATENT DOCUMENTS

WO    WO 99/18232    4/1999

OTHER PUBLICATIONS

ATCC The Global Bioresource Center, http://atcc.org/common/catalog/wordSearch/results.cfm, pp. 1-3. Printed Jul. 3, 2006.*
M. Pezzlo, 1988. Detection of Urinary Tract Infections by Rapid Methods. Clinical Microbiology Reviews, vol. 1, pp. 268-280.*
International Search Report for international application PCT/US03/00655 filed Jan. 9, 2003.
Atlas, R. M. et al., "Handbook of Microbiological Media," Ed. Lawrence C. Parks, CRC Press, Boca Raton 1993.
Baron, E.J. et al., "Manual of Clinical Microbiology," 7th edition, (ed. Murray et al.), ASM Press, Washington DC (1999).
Bonadio, M. et al., "Current Microbiological and Clinical Aspects of Urinary Tract Infection," *Eur. Urol.* 40:439-445 (2001).
Boukadida, J. et al., "Profil Et Sensibilite aux Antibiotiquesde 2063 Bacteries Uropathogenes Isolees Dans Le Centre De La Tunisie," *Bacteriologie*, vol. 2356:8-10 (Sep. 2001).
Braude, A.I. et al., "Infectious Diseases and Medical Microbiology," 2nd Edition, W.B. Saunders Company 292-302 (1986).
"The Difco Manual," 11th Edition, MacConkey Media, p. 288, 1998.
Forbes, B. A. et al., "Diagnostic Microbiology," Ed. Mosby, pp. 350-353, 1998.
Kelly M.T., et al., "Manual of Clinical Microbiology," American Society of Microbiology, pp. 263-277, 1985.
Klauser et al., "Clinical Evaluation of Commercial Reagent Strips for Detection of Significant Bacteriuria in Dogs and Cats," *JAVMA* 37:719-722 (1981).
McKeever P.J. et al., "Use of Cystine, Lactose, Electrolyte-Deficient Medium For Isolation And Identification Of Bacteria And Yeasts From The Skin And Ears of Dogs," *J. Am. Vet. Med. Assoc.* 178(5):489-93 (Mar. 1, 1981).
Navaneeth, B.V., "Urinary Pathogens' Resistance To Common Antibiotics: A Retrospective Analysis," *Tropical Doctor* p. 32 (Jan. 2002).

(Continued)

*Primary Examiner*—Jon P Weber
*Assistant Examiner*—Kailash C Srivastava
(74) *Attorney, Agent, or Firm*—McDonnell Boehnen Hulbert & Berghoff LLP (57) ABSTRACT

The present invention provides devices and methods for determining the presence or absence of pathogens in a biological sample and for the concurrent determination of the antimicrobial susceptibility of pathogens present. The devices and methods of the present invention are able to make the determinations without pre-selection of target bacteria. Instead, all organisms from the sample are applied to the device. In wells where one or more antimicrobial agents are present only pathogens resistant to the antimicrobial agent grow. This allows the user to determine the presence of target pathogens and concurrently determine the resistance patterns of the organisms without the need to subculture the organisms. The present invention also provides methods of performing a business service of performing the determinations described above, and kits containing the devices and descriptions of the methods.

11 Claims, 4 Drawing Sheets

OTHER PUBLICATIONS

Padilla et al., "Effects of Storage Time and Temperature on Quantitative Culture of Canine Urine," *JAVMA* vol. 178(10):1077-1081 (1981).

Perry and Miller, "Umbelliferyl-Labeled Galactosaminide As An Aid In Identification of *Candida Albicans*," *J. Clin. Micro.* 25:2424-2425 (1987).

Staneck, J. L., et al., "Automated Reading of MIC Microdilution Trays Containing Fluorogenic Enzyme Substrates With the Sensititre Autoreader," *J. Clin. Microbiol.* 22:187-191 (1985).

Turnidge, J., et al., "Pathogen Occurrence and Antmicrobial Resistance Trends Among Urinary Tract Infection Isolates in the Asia-Western Pacific Region: Report from the SENTRY Antimicrobial Surveillance Program, 1998-1999, " *Int. Journal of Antim. Agents*, 20:10-17 (2002).

Urban and Jarstrand, "Rapid Determination of the Susceptibility of Bacteria to Antibiotics With "Sensititre" Plates And Nitroblue Tetrazolium," *J. Antimicro. Chem.* 8:363-369 (1981).

* cited by examiner

METHODS AND DEVICES FOR THE DETECTION OF PATHOGENIC MICROORGANISMS AND THEIR ANTIMICROBIAL SUSCEPTIBILITY

This application claims the benefit of U.S. Provisional Application No. 60/347,485, filed Jan. 10, 2002.

FIELD OF THE INVENTION

This invention relates to the field of chemistry, biology, microbiology and business methods for identifying pathogens in mammals, including humans. In particular, it relates to microbiological test methods, compositions, selective media, and devices for determining the antibiotic susceptibility of pathogens obtained from biological samples. The pathogens can be, for example, Gram negative or Gram positive bacteria that can cause skin, ear, urinary tract or other infections in mammals.

BACKGROUND OF THE INVENTION

The following description of the background of the invention is provided simply as an aid in understanding the invention and is not admitted to describe or constitute prior art to the invention.

Bacterial urinary tract infections are common human and veterinary diseases. The enteric Gram negative bacilli normally reside in the intestinal tract and become pathogens when found in the urinary tract; these enteric bacilli are classified in the family of Enterobacteriacae. The primary causative agents of urinary tract infections are Gram negative bacilli. Typically, these include *Escherichia coli, Klebsiella* spp., *Enterobacter* spp., and *Proteus mirabilis*. Infrequently, Gram positive cocci (such as *Staphylococcus aureus* and *Enterococcus faecalis*) and other Gram negative bacteria (such as, *Pseudomonas aeruginosa*) can be urinary pathogens. Other Gram positive cocci (*Staphylococcus, Streptococcus*) and Gram positive bacilli (diphtheroids, *Bacillus subtilis*) are most frequently encountered as normal urethral contaminants.

Bacteriologic testing is commonly performed on patients experiencing symptoms consistent with urinary tract infections. Microorganisms isolated from patients (human and veterinary) are tested to determine the identity of the pathogens and their susceptibility to antibiotics. Information pertaining to minimum inhibitory concentrations (MIC) or the categorical interpretations (susceptible, moderate susceptible, intermediate resistant, or resistant) of antimicrobial agents against an identified pathogen is critical for a medical or veterinary practitioner to confirm or select a proper treatment regime for urinary tract infections.

The clinical effectiveness of antimicrobial chemotherapy for bacterial urinary tract infections requires the correct identification of the causing pathogens and the selection of an appropriate antibiotic treatment regime to eradicate the disease-causing bacteria. The suspect pathogens are isolated by inoculating the specimen onto a culture medium, which is then incubated at 35° C. for 24-48 hours to obtain bacterial growth. The suspect pathogens are then subcultured and their bacterial identity and antimicrobial susceptibility determined by a series of subsequent biochemical tests and standard antimicrobial susceptibility tests.

Methods for routine antimicrobial susceptibility determination of the identified pathogens include the broth dilution method and the agar diffusion assay. The broth dilution method involves the inoculation of a standardized microbiological inoculum (e.g., $1-5 \times 10^5$ cfu/ml) of the pure bacterial isolate in question into a growth medium (typically, a cation-adjusted Mueller Hinton broth) containing a series of predetermined concentrations of a given antibiotic whose MIC is sought to be determined. The inoculated medium is incubated for 18-24 hours and observed for visible growth. The lowest antibiotic concentration that completely inhibits visible growth of the isolated organism as detected by the unaided eye is recorded as the MIC.

The agar diffusion method involves the placement of an antibiotic containing disc or an antibiotic gradient strip on the surface of an agar medium (typically Mueller Hinton agar plate) that has been inoculated with the pure isolate of the microorganism in question. The antibiotic substance then diffuses away from the disc such that the effective concentration of antibiotic varies as a function of the radius from the disc or strip. Thus, the diameter of a resulting no growth area around the disc should be proportional to the MIC.

Procedures to obtain these antibiotic susceptibility data are often time-consuming (48-72 hours), cumbersome, and require highly skilled personnel and expensive automatic equipment. Patients with symptoms of a urinary tract infection (in particular, feline and canine patients) are therefore often treated without regard to bacteriologic findings because of time delays and cumbersome assay procedures required by conventional culture methods. This can compromise the quality of patient care and contribute to the emerging antibiotic resistant bacteria due to the improper use of antibiotics.

Thus, there is need for improved microbiologic tests and antibiotic susceptibility tests, related materials, and related assay devices. If the test procedures could be simplified so that no highly skilled personnel were required for performing the test, and test results were obtained in a shorter period of time, it would facilitate the ability of health care practitioners to confirm or select a proper treatment regime for urinary tract infections. Earlier receipt by health care practitioners (medical or veterinary) of accurate antimicrobial susceptibility information would result in better patient care, and prevent the emerging of antibiotic resistant bacteria due to the improper use of antibiotics.

Furthermore, the use of chromogenic or fluorogenic enzyme substrates have been widely used in a varieties of microbial diagnostic applications. Edberg (U.S. Pat. No. 4,925,789) described a medium containing a nutrient indicator which, when metabolized by target bacteria, releases a moiety which imparts a color or other detectable change to the medium. Chen and Gu (U.S. Pat. No. 5,620,865) used a fluorogenic compound, 4-methylumbelliferyl-β-D-glucopyranoside, in a micro-specific medium for detecting enterococci. Townsend and Chen (U.S. Pat. Nos. 6,387,650 and 6,472,167) described the use of fluorogenic enzyme substrates cocktail to detect bacterial contamination in food products. Koumura et al. (U.S. Pat. No. 4,591,554) describes the use of 4-methylumbelliferyl derivatives fluorogenic analysis to detect and determine the number of microorganisms based on the amount of liberated umbelliferone derivatives. Perry and Miller used an umbelliferyl-conjugated N-acetyl-β-D-galctosaminide for specific identification of a pathogenic yeast, *Candida albicans*, (*J. Clin. Micro.* (1987) 25:2424-2425).

The traditional endpoint of antimicrobial susceptibility determination involves the direct visual or instrument recognition of microbial growth in either a biological matrix, e.g., broth or agar. Urban and Jarstrand used a nitroblue tetrazolium dye to determine the susceptibility of bacteria to antibiotics (*J. Antimicro. Chem.* (1981) 8:363-369). The SENSITITRE.RTM. system uses an instrument capable of automatically reading antimicrobial susceptibility microdilution trays (J. Clin. Microbiol. (1985) 22:187-191). In this procedure, microbial growth and MIC are determined by the measurement of fluorescence produced by bacterial enzyme action on fluorescence substrates. It is disclosed that fluorogenic substrates for this group of bacteria are selected from 7-(N)-(aminoacyl)-7-amido-4-methylcoumarin, 4-methylumbelliferyl noanate, 4-methylumbelliferyl phosphate. Badal et al. (U.S. Pat. No. 5,457,030) disclosed the use of a mixture of fluorogenic substrates consisting of leucine-7-amido-4-methylcoumarin, phenylalanine-7-amido-4-methylcoumarin, and 4-methylumbelliferyl phosphate and a predetermined amount of an antimicrobial susceptibility of the mixture to determine the antimicrobial susceptibility of the majority of clinically significant Gram positive organisms.

All these approaches involve the use of a clone of a bacterial isolate obtained from clinical specimen prior to identification and antimicrobial susceptibility tests. Colonies, i.e., clones, of bacterial cultures, when prepared from the biological specimen, are harvested after a sufficient period of growth. The harvested colony is suspended in a suitable aqueous liquid for biochemical identification and antimicrobial susceptibility test.

Although 90-95% of all urinary infections are caused by a single type of organism, contaminating normal flora are often present on the patient's skin or in the environment, and these organisms can provide an arbitrary contaminant to a urinary sample. Contaminating microflora in a urine specimen are particularly prevalent in veterinary practices relative to medical practice in humans; this is because the specimen collection in veterinary practices tends to be more difficult to control with animals. In general, feline and canine urine specimens can be obtained through a number of means including cystocentesis, catheterization, manual compression of the urinary bladder and natural micturition. Cystocentesis is least likely to introduce microscopic contaminants (including microbial contamination). If the samples are collected by manual compression of bladder or natural micturition, even with the effort of collecting "mid-stream" sample, microbial contamination in the sample is expected. Although cystocentesis is recommended, other methods are often used in veterinarian practices due to the difficulty in controlling the animals. Problems with the contamination of urine specimens have, in the past, prevented accurate assessments of effective antibacterial therapies for urinary tract infections. Accordingly, devices and related methods are needed which distinguish uropathogens from contaminating organisms.

The device and methods disclosed herein represent a departure from traditional microbial test procedures that involve first initiating non-specific growth of pathogens (i.e. bacteria) from a sample, such as by: 1) obtaining a sample on a loop; 2) streaking the sample from the loop on selective media; and 3) growing all pathogens present. After pathogen growth has occurred, one or more colonies would be selected for further inoculation and growth, followed by susceptibility testing against various reagents (i.e. antibiotics) and concentrations of reagents.

U.S. application Ser. No. 08/942,369, filed Jan. 10, 2002, now U.S. Pat. No. 6,984,499, is hereby incorporated by reference in its entirety, including all charts and drawings. In the event a definition explicitly provided herein contradicts a definition provided in the incorporated application, the definition explicitly provided herein shall govern.

SUMMARY OF THE INVENTION

The present invention provides devices and methods for determining the presence or absence of pathogens in a biological sample and for the concurrent determination of the antimicrobial susceptibility of pathogens present. The devices and methods of the present invention are able to make the determinations without pre-selection of target bacteria. Instead, all organisms from the sample are applied to the device. In wells where one or more antimicrobial agents are present (i.e. antibiotics), only pathogens resistant to the antimicrobial agent(s) grow. This allows the user to determine the presence of target pathogens and concurrently determine the resistance patterns of the organisms without the need to subculture the organisms. Further, confirmatory testing of organisms that grow in these wells, if performed, will automatically be restricted to those pathogens that have already exhibited resistance. This therefore enables accurate detection and identification of resistant pathogens because, in the first step of the process, all pathogens present in the sample are presented to the medium. By presenting all pathogens, the likelihood of finding resistant organisms is greatly increased.

By "subculturing" is meant that colonies are isolated from the biological sample and analyzed for identification and/or susceptibility to antimicrobial agents. This production of subcultures generally involves plating of the biological sample on an isolation medium (e.g., MacConkey agar in the case of uropathogens), and isolation of pure colonies for analysis and identification through traditional biochemical tests or other confirmatory tests. The present invention eliminates this requirement. Confirmatory tests are those tests that are performed using subculturing and traditional biochemical tests. Many tests are described in the Manual of Clinical Microbiology, 7$^{th}$ edition, (ed. Murray et al.), ASM Press, Washington DC, (1999) for confirming identity and antimicrobial susceptibility, as well as in other publications known to those of ordinary skill in the art. Susceptibility is preferably determined according to the Kirby-Bauer or Minimum Inhibitory Concetration (MIC) tests. A "colony" is a population of cells growing on solid or semi-solid medium (e.g., plates) and arising from a single colony forming unit. A "colony forming unit" (CFU) is the minimum number of separable cells on the surface of a solid or semi-solid medium (e.g., agar) that gives rise to a visible colony of progeny. CFUs may consist of pairs, chains and clusters as well as single cells.

The Kirby-Bauer test is a disk diffusion antibiotic susceptibility test. The test applies a defined inoculum (compared to McFarland 0.5 OD standard) streaked as a lawn onto a large Mueller-Hinton agar plate in 3 directions to ensure confluence. Antibiotic-impregnated disks are placed onto the agar surface. As the bacteria on the lawn grow, they are inhibited to varying degrees by the antibiotic diffusing from the disk. Zones of inhibition of a certain diameter (which varies for different antibiotics and, to a lesser extent, bacterial species) correlate with sensitivity or resistance to the antibiotic tested.

The present invention therefore provides a multi-compartment assay device for detecting the presence or absence of pathogens in a biological sample. The device also allows for the concurrent determination of the anti-microbial susceptibility of pathogens present in the sample. In various embodiments the pathogens are uropathogens, skin infection organisms, ear infection organisms, or pathogens that are known to cause any disease or condition of medical interest.

In a preferred embodiment the pathogens are the primary Gram-negative uropathogens and the biological fluid is urine.

The devices of the invention have a housing where a plurality of compartments or wells are situated, supported, or present in the housing. The device also has at least one well for determining the presence or absence of pathogens in the sample, which well contains a pathogen specific medium. At least one well contains an antimicrobial susceptibility medium that contains an antimicrobial agent. In a preferred embodiment the device has a well cover window that is connected to a slidable tab, and the slidable tab has open and closed positions. One or more wells or compartments of the device open or close upon movement of the slidable tab from the open to the closed position, or from the closed to the open position, thereby allowing access to the wells or compartments. Growth of organisms can be detected in the wells by a variety of detectable signals, e.g., by a fluorescent signal generated when growth occurs in the well, by a color change caused by a chemical change due to growth in the medium, or another detectable signal. By the well cover window being "connected" to the slidable tab is meant that movement of the slidable tab results in movement of the well cover window. The connection can be directly, as by direct physical contact, or indirectly through another part on the device. In a preferred embodiment the "slidable tab" is a part fashioned to receive pressure, which is transmitted to another part of the device (e.g., the well cover window), such that movement of the slidable tab results in movement of the well cover window.

Growth of organisms in the at least one well for determining the presence or absence of pathogens in the medium and production of a detectable signal indicates the presence of pathogens in the medium. Growth of organisms in the at least one well containing the antimicrobial susceptibility medium and production of a detectable signal indicates that the organisms lack susceptibility to the antimicrobial agent in the well. In the most preferred embodiment the pathogens are the primary Gram negative uropathogens and the pathogen specific medium is a uropathogen specific medium. In other embodiments the pathogens are skin infection organisms or ear infection organisms. The biological fluid is preferably urine.

In preferred embodiments the device also contains a positive control. The positive control can be a well containing a substance or ingredients that provide a detectable signal identifiable with the signal of a well where microbial growth has occurred. The device also preferably includes a negative control. The negative control is preferably a well containing a substance or ingredients that provide a detectable signal identifiable with the signal of a well where microbial growth has not occurred. In one embodiment the signal provided is a fluorescent signal, for example, from 4-methylumbelliferone or a derivative thereof In another embodiment the signal is a colorimetric signal, such as a color (or loss of color) provided by resazurin or methylene blue dyes, derivatives thereof, or other dyes. In the presence of resazurin or methylene blue, bacteria present produce reducing substances which reduce and change the color of the dyes. Resazurin changes from blue-purple to pink when reduced, and methylene blue loses its blue color in the reduced state. Thus, in preferred embodiments a reduced form of the dyes provides the signal. In another embodiment a solution or reagent is added to one or more test wells that increases the signal provided by the ingredients that provide the detectable signal. In one embodiment the wells contain 4-methylumbelliferone and a basic solution is added to the wells to enhance the fluorescent signal provided, thereby facilitating detection. In a preferred embodiment the basic solution is 0.1 M Tris pH 8.5-9.5. While 0.1 M Tris is preferred, other basic solutions can also be used to enhance fluorescence, using different buffers, pH ranges, or concentrations. Basic solutions have a pH greater than 7.0.

By "identifiable with the signal" is meant that a signal can be matched or otherwise associated with a control well, such that interpretation of whether or not growth has occurred in a well and to what extent can be determined based on the comparison with one or both control wells. In various embodiments the compartments of the device are of any shape, but most preferably are a circular or oval configuration. The slidable window member can have an equal number of circular orifices that correspond to the well openings when the window is in the open position. Thus, when the window is in the open position the wells will be open and access will be provided for introducing sample into the wells, e.g., by use of a pipette. Similarly, when the slidable window is in the closed position the wells will be closed and no access will be provided for introducing sample into a well. Of course the person of ordinary skill will realize that embodiments can be created wherein some windows remain open or closed, as needs require.

In another aspect, the present invention provides methods of providing a business service for determining the presence or absence of pathogens in a biological sample and for determining the antimicrobial susceptibility of pathogens present in the sample. In a preferred embodiment the methods include collecting a biological sample, using a multi-compartment assay device to preliminarily determine the presence or absence of pathogens in the biological sample and to concurrently preliminarily determine the antimicrobial susceptibility of pathogens present in the sample, obtaining a result of confirmatory testing of the presence or absence of pathogens in the sample and obtaining a result of confirmatory testing of the antimicrobial susceptibility of pathogens present in the sample. In a preferred embodiment the preliminary determination of the presence or absence of pathogens in the sample and of the antimicrobial susceptibility of pathogens present is performed without performing a sub-culturing step. Thus, with the present invention one can provide the service of determining the presence or absence of pathogens in a biological sample and concurrently determine the antimicrobial susceptibility of pathogens present in the sample. The pathogens can be uropathogens such as the primary Gram negative uropathogens, or can be skin infection organisms, ear infection organisms, or organisms that cause other diseases or medical conditions of interest. The result can be obtained by performing the assays, or by obtaining a result of an assay performed by another person. The multicompartment assay device is preferably a device of the present invention.

By "concurrently" is meant that the preliminary determination of the presence or absence of pathogens in the sample and the determination of the antimicrobial susceptibility of pathogens present occurs simultaneously. A "preliminary determination" is made using a device of the present invention and is made without the use of subculturing. In other embodiments the concurrent preliminary determination and the determination of antimicrobial susceptibility are made within 1 hour, or 2 hours, or 4 hours, or 8 hours, or 12 hours, or 18 hours, or 24 hours of each other. In various embodiments the preliminary determination has a positive predictive value of at least 90%, and a negative predictive value of at least 90%. In various embodiments the determinations have a positive predictive value of at least 92%, 94%, 95%, 97%, or 98%, and a negative predictive value of at least 92%, 95%, 97%, or 98%. "Positive predictive value" refers to the ability to correctly identify the presence of pathogens in the sample and whether or not they are susceptible to one or more specific antimicrobial agents, when compared with results of confirmatory testing. "Negative predictive value" refers to the ability to correctly identify the absence of pathogens in the sample when compared with results of confirmatory testing, and/or to the ability to correctly identify when organisms are not susceptible to one or more specific antimicrobial agents, when compared with results of confirmatory testing. The predictive values are expressed as a percent, which indicates the degree of confidence that the result is not due to randomness. Persons of ordinary skill in the art are familiar with statistical methods for determining degrees of confidence, variance, and standard deviation.

The person of ordinary skill will realize there are various embodiments of these methods. For example, one can simply obtain the results of confirmatory testing performed by others rather than perform the confirmatory testing themselves. In a preferred embodiment the biological sample is collected at a point of care facility and the preliminary determination of the presence or absence of uropathogens in the sample is performed at the point of care facility. In one embodiment the confirmatory testing of the presence or absence of primary Gram negative uropathogens in the sample and of the antimicrobial susceptibility of pathogens present is performed at a secondary testing laboratory. In a preferred embodiment the secondary testing laboratory is located off site from the point of care facility. Thus, the biological sample is introduced into wells of the device and the device incubated and a result determined at the point of care facility prior to sending the device to a secondary testing laboratory for confirmatory testing. A course of treatment is preferably determined based on the result determined at the point of care facility, before or after sending the device to the secondary testing laboratory. In a preferred embodiment the device is sent to a secondary test laboratory with the biological sample contained in at least one well of the device. The confirmatory testing performed at the secondary testing facility can be reported to the point of care facility. Follow up treatment or changes in course of treatment can be decided based on the result from the secondary testing laboratory.

By "off site" is meant a physical location outside of the laboratory of the point of care facility. The laboratory of the point of care facility is the location (or locations) where the preliminary determination of the presence or absence of uropathogens in the sample is made. In a preferred embodiment the "off site" location of the secondary testing laboratory will be located at a facility directed by a business organization other than the organization directing the point of care facility.

The present invention also provides kits including a multicompartment assay device for detecting the presence or absence of pathogens in a biological sample and for concurrently determining the antimicrobial susceptibility of pathogens present provided in a package. In various embodiments the kits include a device of the invention (preferably enclosed in a moisture impervious enclosure) and any combination of the following items, and can include more than one of any particular item: at least one bottle containing a diluent solution for diluting a fluid sample to be tested; at least one pipette for transferring fluid sample from one container to another; at least one pipette for transferring the biological sample from one container to another; at least one container of a substance that increases a fluorescent signal when added to a well of the device; at least one container of a substance that increases a colorimetric signal when added to a well of the device; at least one container of a basic solution; a sealable plastic bag for enclosing and incubating the device after application of sample and diluent; instructions for use of the assay device and kit materials. All of the kits optionally contain instructions for using the assay device, including instructions for applying a sample suspected of containing uropathogens to the device, and instructions for using the pipette to add sample to the diluent bottle. The kits preferably contain an outer enclosure enclosing the assay device and any other members of the particular kit, if present.

In a preferred embodiment the kit contains an assay device of the present invention enclosed in a moisture impervious enclosure, at least one bottle containing a diluent solution for diluting a fluid sample to be tested, at least one pipette for transferring fluid sample from one container to another, a sealable plastic bag for enclosing and incubating the device after application of sample/diluent; and instructions for use of the assay device.

In another embodiment the kit contains an assay device of the invention enclosed in a a moisture impervious enclosure, instructions for applying a sample suspected of containing uropathogens to the device, at least one pipette, at least one container of a substance that increases a fluorescent signal when added to a well of the device or at least one container of a substance that increases a colorimetric signal when added to a well of the device; and optionally contains an outer enclosure enclosing the kit components. In one embodiment the container of a substance that increases a fluorescent signal when added to a well of the device contains a basic solution. The pipettes of the kits are preferably disposed within the outer enclosure when the outer enclosure is present, and the instructions can instruct a user to use the pipette to add sample to the diluent bottle.

In another aspect the present invention provides methods for determining antibiotic resistance of microorganisms. The methods involve inoculating a clinical or biological sample to an antimicrobial susceptibility interpretation medium, wherein no step of subculturing is performed prior to the step of inoculating. The sample and medium are incubated, whereby growth of microorganisms in the medium indicates that the microorganisms lack susceptibility to and are resistant to the antimicrobial agent(s) present in the medium. The clinical or biological samples can be diluted prior to the inoculation, e.g., with saline solution or another appropriate diluent. In other embodiments, the sample can be placed in an antimicrobial susceptibility medium and incubated to grow pathogens that may be present. Thus, resistance to antimicrobial agents (e.g., antibiotics) contained in the medium can be determined.

The summary of the invention described above is not limiting and other features and advantages of the invention will be apparent from the following detailed description of the preferred embodiments, as well as from the claims.

DETAILED DESCRIPTION OF THE INVENTION

The multi-compartment assay device of the present invention allows for the determination of the presence or absence of pathogens in a test sample and the concurrent determination of the antimicrobial susceptibility of pathogens present. In various embodiments the pathogens are the primary Gram negative uropathogens, skin infection organisms, ear infection organisms, or another group of organisms that cause a disease or condition of medical interest.

By "primary Gram negative uropathogen" is meant the group of Gram negative bacteria that cause at least 80% of the human and veterinary urinary tract infections. This group includes, but is not limited to, *Escherichia coli, Kiebsiella* spp., *Enterobacter* spp., and *Proteus mirabilis*. In other embodiments subsets of the primary Gram negative uropathogens can be detected. Thus, in these embodiments at least 90% of the primary Gram negative uropathogens can be detected, or at least 95%, or 85%, or 80% or 75% or 70% of the primary Gram negative uropathogens are detected. In a particularly preferred embodiment the primary Gram negative uropathogens include the group of organisms including: *Escherichia coli, Kiebsiella* spp., *Enterobacter* spp., *Serratia* spp., *Proteus* spp., *Citrobacter* spp., *Acinetobacter* spp., *Providencia* spp., *Morganella morganii*, and *Salmonella enterica*. In other embodiments additional Gram negative rods are included in the group.

By "pathogen-specific medium" is meant a medium that allows for the substantial growth of only the target pathogen(s) and for substantially less growth of any other bacteria, and for generation of a detectable signal when such growth occurs. Growth that is "substantially less" does not generate a detectable signal to an extent that the result of the assay is changed. Target pathogens are those microorganisms whose presence or absence and antimicrobial susceptibility is sought to be determined. In various embodiments target pathogens include the primary Gram negative uropathogens, skin infection organisms, ear infection organisms, or other target pathogens.

By "uropathogen specific medium" is meant a medium that allows for the substantial growth of the primary Gram negative uropathogens and for generation of a detectable signal when such growth occurs. The medium allows for substantially less growth of any other bacteria. Growth that is "substantially less" does not generate a detectable signal to an extent that the result of the assay is changed.

In addition to detecting primary Gram negative uropathogens the device of the present invention also allows for the concurrent determination of the antimicrobial susceptibility of primary Gram negative uropathogens present.

By "skin infection organisms" is meant the group of bacteria that cause at least 80% of the human and veterinary skin infections.

By "ear infection organisms" is meant the group of bacteria that cause at least 80% of the human and veterinary ear infections.

By "antimicrobial susceptibility" is meant the organisms response to the presence of an antimicrobial agent. Antimicrobial agents are compounds that kill bacteria or inhibit their growth. Thus, antibiotics are antimicrobial agents. Various antibiotics and antimicrobial agents are described in WO-9948232 U.S. Pat. No. 6,984,499. The antimicrobial susceptibility can be determined by evaluating whether growth and signal generation have occurred in a particular medium containing an antimicrobial agent. If growth and signal generation occurs in the uropathogen specific medium but no significant growth and signal generation occurs in the antimicrobial susceptibility medium, the conclusion is the primary Gram negative uropathogens are present and are vulnerable to the antimicrobial agent present in the compartment.

By "antimicrobial susceptibility medium" is meant a medium that allows the category of interpretation (e.g., susceptible, moderately susceptible, intermediate susceptible, intermediate resistant, or resistant) of a detected target microbial organism relative to an antimicrobial agent or combinations thereof. These media are comprised of all components of the target organism specific media, such as the uropathogen specific medium, as well as a predetermined amount of an antimicrobial agent. For example, when the target microbial organisms are uropathogens, the antimicrobial susceptibility medium detects the susceptibility of the target organisms toward an antibiotic; the antimicrobial susceptibility medium can detect antimicrobial efficacy of one or more antibiotics toward the primary Gram negative urinary pathogens.

By "point of care facility" is meant the place where a mammalian patient is met by a health care practitioner (e.g., medical doctor, veterinarian, medical assistant, physician's assistant, nurse, etc.) for medical evaluation and diagnosis. Usually this will mean the office of a physician or veterinarian. In the case of animal care, a veterinarian's clinical office where animal patients are met and medically evaluated is a point of care facility, as is an animal hospital. A point of care facility can also be the farm, stable, or barracks where the animal is kept, especially in the case of large animals, as this is the location where the animal caretaker will meet the animal for medical evaluation and diagnosis. In the case of human care, the medical office of a doctor, or a hospital is a point of care facility as this is where the patient meets a health care practitioner for medical evaluation and diagnosis.

A "secondary testing laboratory" is a laboratory where clinical samples are evaluated using confirmatory subculturing methods to ascertain the identity of microorganisms present in the sample. Normally the secondary testing laboratory will be off site from the point of care facility, and normally will be a commercial testing laboratory where clinical samples are sent for evaluation by subculturing methods.

One advantage of the present invention is that a doctor, veterinarian, or other health care practitioner is able to determine with a high degree of confidence and within only 24 hours whether or not a urinary tract infection is present that is caused by a primary Gram negative uropathogen.

Another clear advantage of the present invention is the ability to concurrently test for antimicrobial susceptibility and/or antibiotic resistance of pathogens in a test sample without the usual need for sub-culturing procedures. Such sub-culturing procedures generally include: inoculating a sample into a medium to facilitate the growth of pathogens; isolation of colonies from the medium; and performing identity tests on the separate colonies. Thus, within only 24 hours it can be determined whether a primary Gram negative uropathogen is present and, if so, which antimicrobial substance can be used to effectively treat the infection.

While sub-culturing procedures provide useful information, they are typically not performed at a point of care facility, i.e. at the doctor's or veterinarian's office. They are also relatively time consuming and labor intensive. Therefore, prior to the present disclosure, a health care practitioner or animal caretaker would typically collect biological samples (e.g., urine) and send the samples off-site to have pathogens identified and their antimicrobial susceptibility determined by subculturing procedures. As such, without an initial indication of pathogen presence or pathogen susceptibility, a course of treatment would either be delayed or, if started before obtaining subculturing results, could be either unnecessary or ineffective for the particular pathogen present. The well cover window of the present invention provides a convenient method of closing the wells and inhibiting evaporation. The device is preferably transferred to a secondary testing laboratory in a sealed bag and with the well cover window in the closed position.

Through the use of the devices and methods described herein, the health care practitioner (e.g., doctor or veterinarian) or animal caretaker is able to: obtain a sample from a patient; apply the sample to the device; incubate the device on-site; read the device on-site; recommend a course of treatment (if necessary); and, optionally, send the device to a secondary testing laboratory for confirmatory testing, such as sub-culturing, wherein the results of the subculturing and/or antimicrobial susceptibility are reported back to the point of care facility or health care practitioner from the secondary testing laboratory. The device can be sent to the secondary testing laboratory by any suitable means, such as ground transportation (mail, courier, etc. . . . ) or by air, and can be physically transferred to the facility. As such, the ability of the health care practitioner to make an earlier, educated decision on proper treatment is enhanced. The health care practitioner can also timely modify the course of treatment prescribed based on the results of the assay device if a course of treatment was prescribed prior to reading confirmatory testing at the secondary testing laboratory. Also, through the use of the device, an efficient means for transporting the patient's sample to the secondary testing laboratory is provided.

EXAMPLE 1

Figure 1:
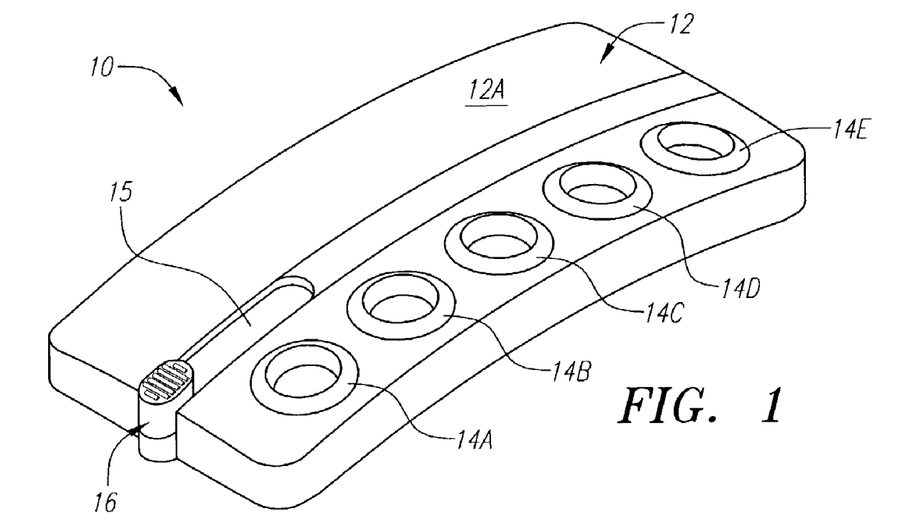
FIG. 1 is a top, perspective view of a preferred device of the present disclosure.
Figure 2:
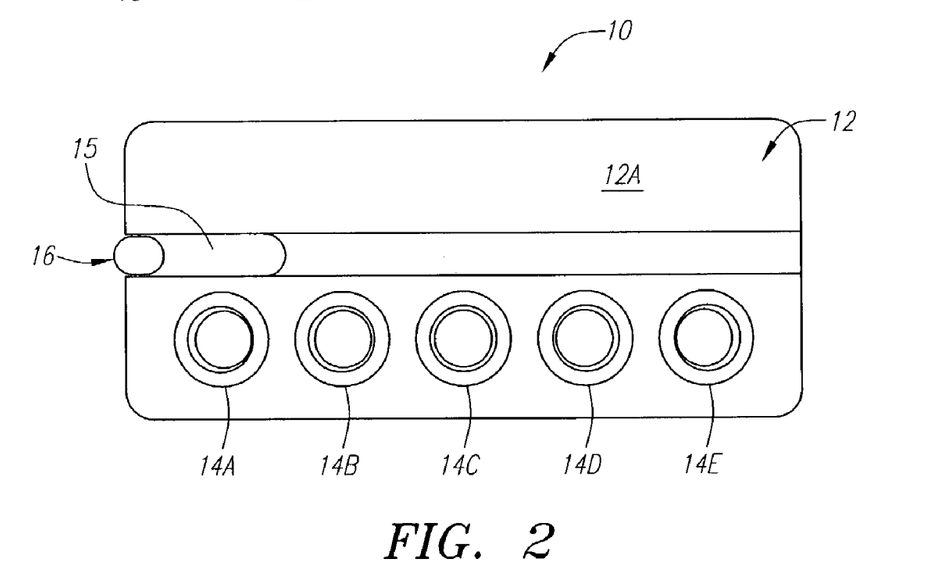
FIG. 2 is a top, plan view of the device of FIG. 1.
Figure 3:
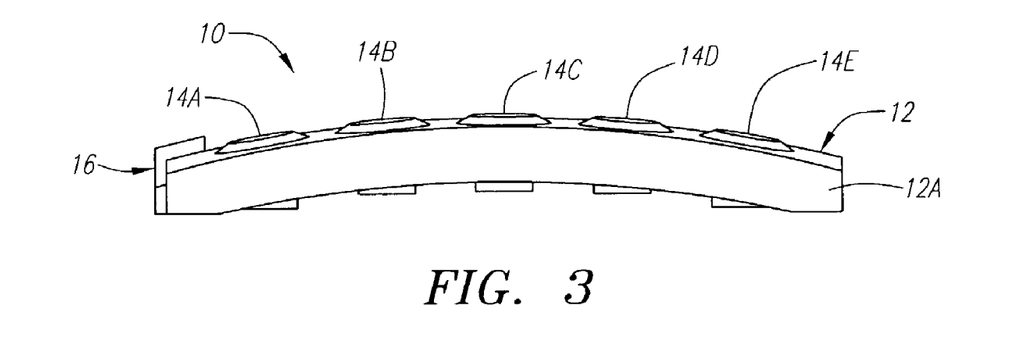
FIG. 3 is a side, elevational view of the device of FIG. 1.
Figure 4:
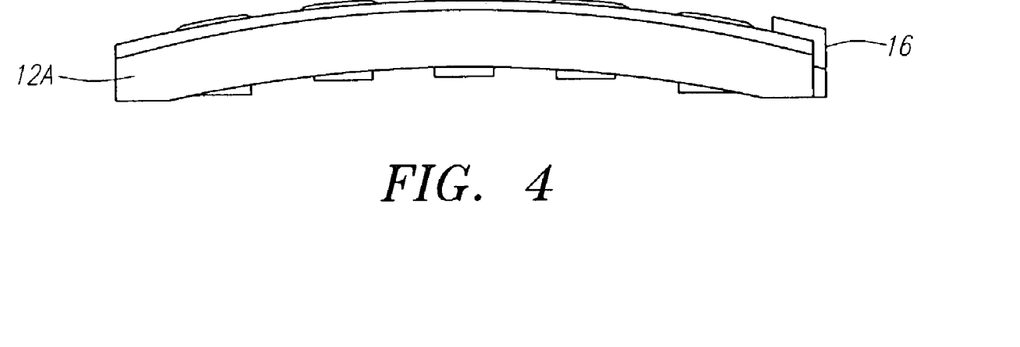
FIG. 4 is a side, elevational view of the device of FIG. 1.
Figure 5:
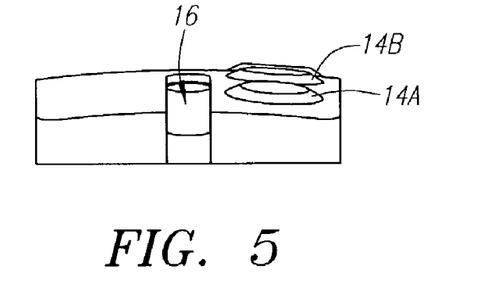
FIG. 5 is an end, elevational view of the device of FIG. 1.
Figure 6:
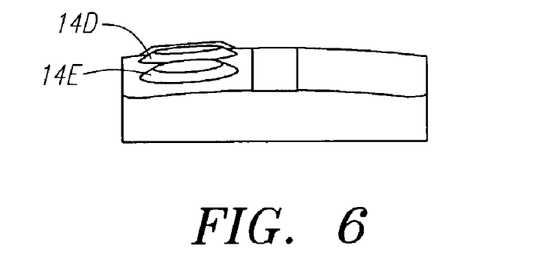
FIG. 6 is an end, elevational view of the device of FIG. 1.
Figure 7:
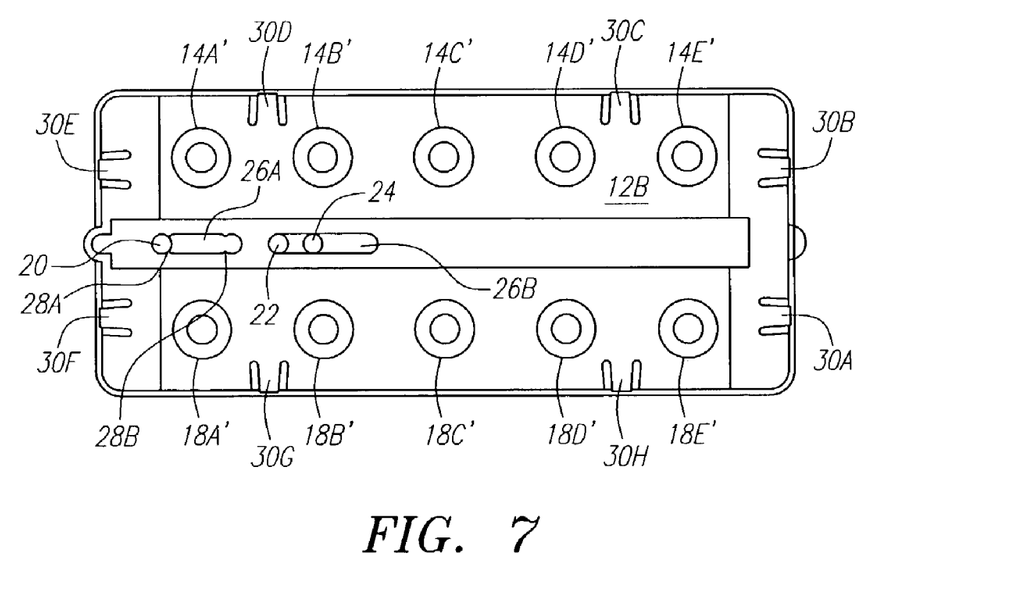
FIG. 7 is a bottom, plan view of the device of FIG. 1.
Figure 8:
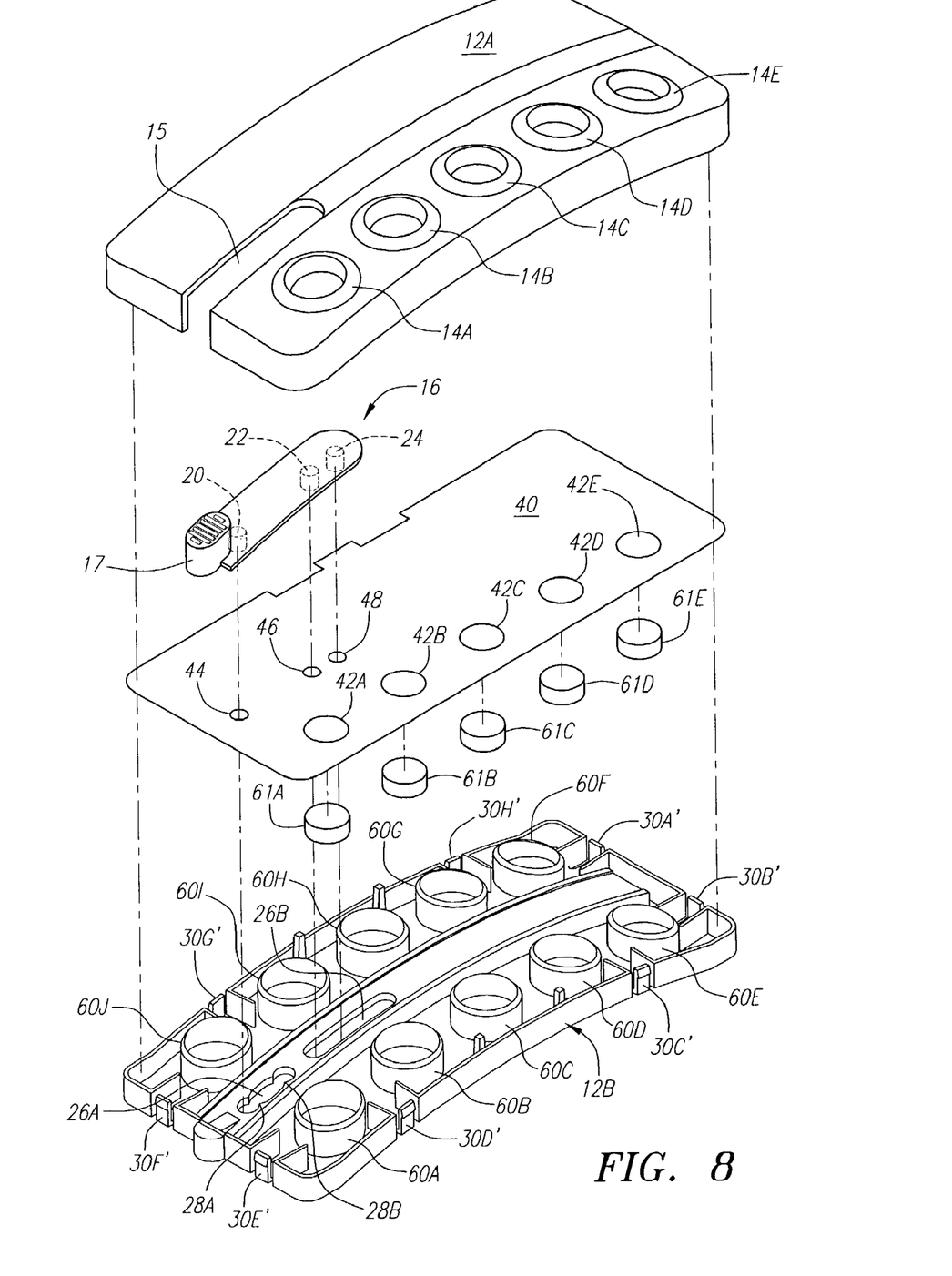
FIG. 8 is an exploded, perspective view of the device of FIG. 1.

The following example illustrates one embodiment of the device of the present invention. The person of ordinary skill in the art will realize that other variations and embodiments of the device described may also be useful. Turning to the Figures, device 10 includes a housing 12 having upper and lower housing portions 12A and 12B, respectively. Housing 12 is preferably fabricated from a material that is light and easily manufacturable, such as plastic or another mold-injectable substance, e.g., polystyrene. Upper housing 12A has well openings 14A-14E and slot 15 for movement of slidable tab 16 relative to the housing. While five well openings (or "compartments") are shown, a fewer or greater number of openings can be provided, such as for different reagents or for positive and negative controls (discussed, below). Lower housing 12B has wells 60A-60J, wherein wells 60A-60E correspond to well openings 14A-14E in upper housing 12A. Lower housing 12B also includes locking tabs 30A-30H having locking tab protrusions 30A'-30H'. The locking tabs can be spread out between the two sides of the housing and/or on the proximal and distal ends of the device. As shown in FIGS. 7 and 8, the upper and lower housing are joined by engaging locking tabs 30A-30H with upper housing 12A. The upper and lower housings 12A and 12B can also be joined or otherwise reinforced by other means, such as, for example, welding and/or gluing. The device can also be manufactured as one unitary portion. Lower housing 12B also has slots for interacting with tab 16. More specifically, slot 26A receives tab guide 20 and slot 26B receives tab guides 22 and 24. Slot 26A further has two restrictions, 28A and 28B for providing resistance when the tab is positioned in the open and closed positions, respectively.

Disposed in device 10 are slidable tab 16, well cover window 40 and pads 61A-E. The slidable tab is present on the proximal end of the device. Slidable tab 16 has tab protrusion 17, primary tab guide 20, secondary tab guide 22 and tertiary tab guide 24. Slidable tab is preferably a moldable, plastic material, i.e., polypropylene. Well cover window 40 has orifices 44, 46 and 48 for receiving tab guides 20, 22 and 24, respectively, and well orifices 42A-42E. Window 40 is preferably a thin, see-though, non-fluorescing material, e.g., a polyester such as polyethylene terephthalate glycol (PETG) or another suitable plastic. Pads 61A-E are disposed in well 60A-E and are preferably manufactured from an absorbent material (e.g., synthetic or natural fibers). In a most preferred embodiment, pads 61A-B are cotton fibers, are between about 8 to about 10 mm in diameter and have a thickness of between about 0.5 to about 2 mm. Pads 61A-B are suitable for use with reagents, such as those disclosed in U.S. Pat. No. 6,984,499. In other embodiments more than one slidable tab may be present, with each slidable tab controlling a specific well or group of wells. Alternatively, the well cover window may be provided as one or more tabs, plates, or section of material that can detach from the device or can be raised or lowered on a hinge of the device, thereby providing access to the wells. Each tab, plate, or section can cover a single well or multiple wells. In yet another embodiment the tab and well cover window can be formed as a unitary part instead of having orifices for receiving tab guides.

In operation of the preferred embodiment illustrated, well cover window 40 is positioned in the "open" position, by positioning tab 16 such that primary tab guide 20 is proximal to 28A in slot 26A. In this position, the user can access pads 61A-E, disposed in wells 60A-E, through upper housing well openings 14A-E, such that a biological sample can be introduced into any or all of wells 60A-E. After sample is applied, the user can move window 40 to the "closed" position by sliding tab 16 such that primary tab guide 20 is positioned distal to 28B in slot 26A.

Figure 9:
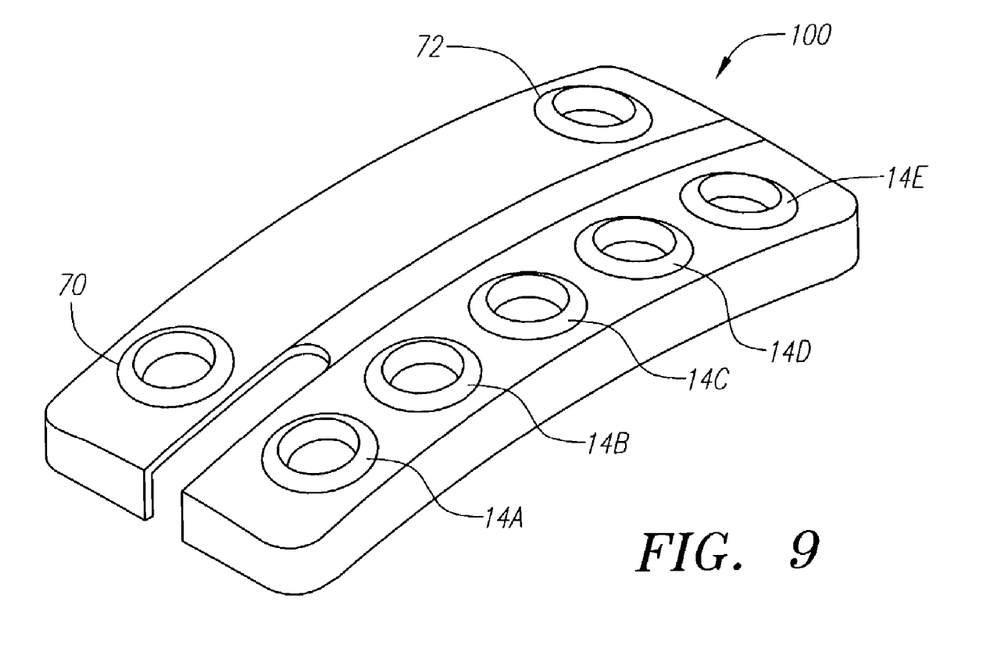
FIG. 9 is a top, perspective view of an alternate preferred embodiment of the device of the present disclosure featuring optional positive and negative control wells.

In an alternate embodiment, positive and negative control wells can be disposed in the device. With reference to FIG. 9, device 100 is substantially similar to device 10, however, device 100 has wells 70 and 72 as positive and negative controls, respectively. Device 100 also can have corresponding window orifices (not shown) that align with wells 70 and 72 when the window is in the "open" position.

Negative control well 72 preferably includes a substance or ingredients resembling or identifiable with the signal of a well where microbial growth has occurred. The resemblance can be that a detectable signal (e.g., the color of the substance or ingredients, correspondence of a fluorescent signal, etc) in the negative control well that substantially corresponds to the signal of a sample in a well where growth has not occurred. In a preferred embodiment, an absorbent pad in negative control well 72 is treated with about 20 microliters of negative control solution having the following ingredients: Coomassie Brilliant Blue G (0.012-0.016%), Bile Salt #3 (3.75 grams/liter), Casein Peptone (50 grams/liter) and Amphotericin B (0.055 grams/liter) with or without HEPES buffer.

Positive control well 70 preferably includes a substance or ingredients that resemble the appearance of wells 14A-E when they are positive for pathogenic substances. The resemblance can be that a detectable signal is provided by the control well that is identifiable with the signal of a well where microbial growth has occurred. For example, the color of the substance or ingredients in the positive control well can substantially correspond to the color of a sample in a well where growth has occurred, or a fluorescent signal can correspond to the wells. In a preferred embodiment, an absorbent pad in positive control well 70 is treated with about 20 microliters of: Coomassie Brilliant Blue G (0.012-0.016%), bile salt #3 (3.75 grams/liter), casein peptone (50 grams/liter), amphotericin B (0.055 grams/liter) and 4-methylumbelliferone, free acid (0.05-0.10 grams/liter). By having positive and negative controls directly on the device and in visual proximity to the other test wells, the ability for the user to make correct determination of the presence or absence of a positive signal from the test wells is enhanced.

In other embodiments the positive and negative controls need not be situated directly in a well, but can also be position on the housing of the device, or included on a separate card, or included as liquids or solids separate from the device, such as a color or fluorescent standard that can be provided with the device. The precise form of the controls is not critical, but they should provide a clear reference from which a result can be determined.

EXAMPLE 2

In this example a further embodiment of the present invention is disclosed that includes a kit for performing the one or more assays. The kit can include any combination of the following items: an assay device of the present invention; an outer box; a sealed, foil pouch enclosing each device 10 or 100; and optionally, a desiccant within each pouch; a sample diluent bottle; pipette(s) (preferably two per device, one for facilitating transfer of the sample to the diluent bottle (this pipette can be enclosed with the device in the foil pouch) and one for facilitating transfer of sample/diluent to the device); sealable plastic bag(s) for enclosing and incubating the device after application of sample/diluent; and instructions for use of the kit/device. Any or all of these items may be provided in a package (e.g., a box, pouch, envelope, or other suitable package or enclosure) as a kit.

Exemplary instructions for using device 10 or 100, and kits containing such devices and instructions can be provided. In one embodiment, the instructions read as follows:

For each specimen to be tested, remove one foil package, one sample diluent bottle, one sterile wrapped device pipette, and one sealable plastic bag from kit box. Remove the test device from the foil package. Leave the sample pipette in the foil bag until ready to transfer the specimen. Label the device and sample diluent bottle with the patient identification.

Loosen cap on the diluent bottle for easier handling during the sample transfer step.

Using the sample pipette provided in the foil bag, carefully transfer a pre-specified amount of the specimen into the sample diluent bottle (i.e. four drops if a urine specimen or other specimen prepared using known techniques). Hold the sample pipette vertically while dispensing the sample into bottle.

Tightly cap the sample diluent bottle and mix thoroughly by inverting several times.

Place the test device on a flat surface. Verify that the device windows are in the open position. Care must be taken not to touch or contaminate the open wells with fingers, etc., prior to running the test.

Uncap the sample diluent bottle. Open the sterile wrapped device pipette and draw sample/diluent mixture up into the pipette. Holding device pipette vertically over the center of a well, place a pre-specified amount of sample/diluent to the well (i.e. two drops of sample/diluent—in some embodiments dilution of sample is unnecessary). Repeat for each remaining well, refilling the pipette if necessary.

Slide the movable tab to close the test well windows.

Insert each device into a separate sealable plastic bag (included with the kit). Seal bag tightly to prevent dehydration during the incubation step.

Incubate the sealed device at 35° C. for 24 hours. In one embodiment the instructions also include the step of opening the plastic bag and applying a fluorometric or colorimetric signal enhancing agent.

Do not remove device from sealable plastic bag. Read the test results by placing a 6 watt 365 nm UV lamp 6 to 12 inches above the test device. Be careful not to look directly at the UV source while reading the test results.

Fluorescence in a sample well (other than the positive control well, if present) indicates pathogen growth. As set forth in U.S. Pat. No. 6,984,499, signals or lack thereof are indicative of susceptibility to antibiotics predisposed in the wells or lack of susceptibility.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An assay device for detecting the presence or absence of uropathogens that are the primary causative agents of urinary tract infections in a biological sample and for concurrently determining the anti-microbial susceptibility of the uropathogens present in the sample, comprising:
    a housing comprising a plurality of wells;
    at least one well comprising a uropathogen specific medium;
    at least one well comprising an antimicrobial susceptibility medium comprising an antimicrobial agent; and
    a lower housing portion comprising the at least one well, an upper housing portion having openings over the at least one well, and a well cover window slidably positioned between the upper housing portion and the lower housing portion, wherein the well cover window has an open position for providing access to the wells and a closed position for closing the wells;
    wherein growth of primary causative agents of urinary tract infections and production of a detectable signal in the at least one well comprising a uropathogen specific medium indicates the presence of primary Gram negative uropathogens causative agents of urinary tract infections in the sample; and
    wherein growth of primary causative agents of urinary tract infections and production of a signal in the at least one well comprising an antimicrobial susceptibility medium indicates that the primary causative agents of urinary tract infections lack susceptibility to the antimicrobial agent.

2. The device of claim 1, wherein the uropathogen specific medium is retained on an absorbent pad, and the antimicrobial susceptibility medium is retained on an absorbent pad.

3. The assay device of claim 1, wherein the uropathogen specific medium is specific for primary causative agents of urinary tract infections selected from the group consisting of: *Escherichia coli, Klebsiella* spp., *Enterobacter* sp., *Serratia* spp., *Proteus* spp., *Citrobacter* spp., *Acinetobacter* spp., *Providencia* spp., *Morganella morganii*, and *Salmonella enterica*.

4. The assay device of claim 1, further comprising a positive control.

5. The assay device of claim 4, wherein the positive control comprises a material that generates a signal when growth of a primary causative agent of urinary tract infections has occurred.

6. The assay device of claim 1, further comprising a negative control.

7. The assay device according to claim 1, wherein growth of primary causative agents of urinary tract infections in the wells is indicated by a fluorescent signal.

8. The assay device according to claim 1, wherein the detectable signal is a colorimetric signal generated by resazurin or methylene blue.

9. The assay device according to claim 1, wherein each of the wells have a circular configuration and the well cover window has at least an equal number of circular orifices that correspond to the well openings when the window is in the open position.

10. The assay device of claim 6, wherein the negative control comprises a material that generates a signal when growth of a primary causative agent of urinary tract infections has not occurred.

11. The assay device according to claim 7, wherein the fluorescent signal is generated by 4-methylumbelliferone.

* * * * *